(12) United States Patent
Yao et al.

(10) Patent No.: US 12,268,494 B2
(45) Date of Patent: Apr. 8, 2025

(54) METHOD AND DEVICE FOR OBTAINING SAFE INTERVAL OF HUMAN BODY PARAMETER IN BUILT ENVIRONMENT, TERMINAL DEVICE, AND STORAGE MEDIUM

(71) Applicant: Chongqing University, Chongqing (CN)

(72) Inventors: Runming Yao, Chongqing (CN); Shaoxing Zhang, Chongqing (CN); Chenqiu Du, Chongqing (CN); Baizhan Li, Chongqing (CN)

(73) Assignee: Chongqing University, Chongqing (CN)

( * ) Notice: Subject to any disclaimer, the term of this patent is extended or adjusted under 35 U.S.C. 154(b) by 648 days.

(21) Appl. No.: 17/579,362

(22) Filed: Jan. 19, 2022

(65) Prior Publication Data
US 2023/0181056 A1    Jun. 15, 2023

(30) Foreign Application Priority Data
Dec. 13, 2021 (CN) .......................... 202111518971.1

(51) Int. Cl.
*A61B 5/11* (2006.01)
*A61B 5/00* (2006.01)
(Continued)

(52) U.S. Cl.
CPC ........ *A61B 5/1116* (2013.01); *A61B 5/02405* (2013.01); *A61B 5/1128* (2013.01);
(Continued)

(58) Field of Classification Search
CPC ... A61B 5/1116; A61B 5/1128; A61B 5/1176; A61B 5/02405; A61B 5/02416;
(Continued)

(56) References Cited

U.S. PATENT DOCUMENTS

2008/0275349 A1 *  11/2008  Halperin ................ A61B 5/447
                                                    600/364
2011/0257527 A1 *  10/2011  Suri ......................... G06T 7/13
                                                    600/440

(Continued)

FOREIGN PATENT DOCUMENTS

CA      2927036 A1    4/2015
CN    102114322 A     7/2011
(Continued)

OTHER PUBLICATIONS

Zacharatos et al., "Automatic Emotion Recognition Based on Body Movement Analysis," IEE Computer Graphics and Applications, 2014, p. 35-45. (Year: 2014).*

(Continued)

*Primary Examiner* — Siamak Harandi
*Assistant Examiner* — Daniella M. DiGuglielmo
(74) *Attorney, Agent, or Firm* — Westbridge IP LLC

(57) ABSTRACT

Disclosed are a method and a device for obtaining a safe interval of a human body parameter in a built environment, a terminal device, and a storage medium. The method includes: obtaining a first facial image, a benchmark human body parameter, and a human body posture analysis result of a target user in a target built environment; inputting the first facial image into an emotion analysis model to obtain an emotion analysis result; and obtaining the safe interval of the human body parameter of the target user according to the emotion analysis result, the human body posture analysis result, and the benchmark human body parameter.

8 Claims, 4 Drawing Sheets obtaining a first facial image, a benchmark human body parameter, and a human body posture analysis result of a target user in a target built environment — S11 inputting the first facial image into an emotion analysis model to obtain an emotion analysis result — S12 obtaining the safe interval of the human body parameter of the target user according to the emotion analysis result, the human body posture analysis result, and the benchmark human body parameter — S13

(51) Int. Cl.
  *A61B 5/024* (2006.01)
  *A61B 5/1171* (2016.01)
  *A61B 5/16* (2006.01)

(52) U.S. Cl.
  CPC ............ *A61B 5/1176* (2013.01); *A61B 5/165* (2013.01); *A61B 5/7264* (2013.01); *A61B 5/7296* (2013.01); *A61B 5/0077* (2013.01); *A61B 5/02416* (2013.01)

(58) Field of Classification Search
  CPC ..... A61B 5/165; A61B 5/7264; A61B 5/7296; A61B 5/0077
  See application file for complete search history.

(56) References Cited

U.S. PATENT DOCUMENTS

| | | | |
|---|---|---|---|
| 2013/0190635 A1 | 7/2013 | Shen et al. | |
| 2014/0161421 A1* | 6/2014 | Shoemaker | G11B 27/28 386/278 |
| 2020/0311388 A1* | 10/2020 | Xiang | A61B 5/02416 |

FOREIGN PATENT DOCUMENTS

| | | |
|---|---|---|
| CN | 103530501 A | 1/2014 |
| CN | 105996993 A | 10/2016 |
| CN | 106491117 A | 3/2017 |
| CN | 107595254 A | 1/2018 |
| CN | 108805087 A | 11/2018 |
| CN | 108926338 A | 12/2018 |
| CN | 109657582 A * | 4/2019 ......... G06K 9/00302 |
| CN | 109770851 A | 5/2019 |
| CN | 110621228 A | 12/2019 |
| CN | 110680351 A | 1/2020 |
| CN | 110765838 A | 2/2020 |
| CN | 111143615 A | 5/2020 |
| CN | 112386244 A | 2/2021 |
| CN | 113140312 A | 7/2021 |
| CN | 113326781 A | 8/2021 |
| CN | 113468983 A * | 10/2021 |
| CN | 113627396 A * | 11/2021 |
| CN | 113744878 A | 12/2021 |
| GB | 2582633 A | 9/2020 |
| WO | 2012073016 A1 | 6/2012 |
| WO | 2019144926 A1 | 8/2019 |
| WO | 2019184125 A1 | 10/2019 |
| WO | 2020238023 | 12/2020 |

OTHER PUBLICATIONS

Fang et al., Thermal comfort and skin temperature responses to the supplied, Indoor and Built Environment, 2018, 27 (6), pp. 831-845, dated Jul. 4, 2018.

First Office Action issued in counterpart Chinese Patent Application No. 202111518971.1, dated Aug. 23, 2023.

Li et al., Biological experiment study of indoor environment on thermal comfort and thermal health objective evaluation, HV&AC, 2016, 46(5), pp. 94-100, dated May 15, 2016.

Yao et al., A 'heart rate'-based model (PHSHR) for predicting personal heat stress in dynamic working environments, Building and Environment, 2018, pp. 318-329, dated May 1, 2018.

* cited by examiner

METHOD AND DEVICE FOR OBTAINING SAFE INTERVAL OF HUMAN BODY PARAMETER IN BUILT ENVIRONMENT, TERMINAL DEVICE, AND STORAGE MEDIUM

CROSS-REFERENCE TO RELATED APPLICATIONS

This application claims priority to Chinese Patent Application No. 202111518971.1, filed on Dec. 13, 2021, the entire disclosure of which is incorporated herein by reference.

TECHNICAL FIELD

The present disclosure relates to the technical field of human body data monitoring, in particular to a method and a device for obtaining a safe interval of a human body parameter in a built environment, a terminal device, and a storage medium.

BACKGROUND

Human body parameters are one of the important indicators to measure a person's physiological state. Continuous monitoring of human body parameters helps to control and prevent cardiovascular diseases and other chronic diseases.

In the related art, a benchmark human body parameter is set for the user according to the user's exercise state, so as to determine the user's health condition by using the comparison result of the benchmark human body parameter and the user's actual human body parameter.

However, with the existing human body parameter measurement method, the accuracy of the obtained reference body parameter is low.

SUMMARY

The main objective of the present disclosure is to provide a method and a device for obtaining a safe interval of a human body parameter in a built environment, a terminal device, and a storage medium, which aims to solve the technical problem of low accuracy of obtaining results in the safety interval of human body parameters in the built environment in the prior art.

In order to achieve the above objective, the present disclosure provides a method for obtaining a safe interval of a human body parameter in a built environment, including following operations:
  obtaining a first facial image, a benchmark human body parameter, and a human body posture analysis result of a target user in a target built environment;
  inputting the first facial image into an emotion analysis model to obtain an emotion analysis result; and
  obtaining the safe interval of the human body parameter of the target user according to the emotion analysis result, the human body posture analysis result, and the benchmark human body parameter.

In an embodiment, there are a plurality of the first facial images, before the operation of inputting the first facial image into an emotion analysis model to obtain an emotion analysis result, the method further includes:
  converting the plurality of first facial images into a plurality of grayscale images;
  extracting a facial emotion image corresponding to a region of interest of facial emotion from each of the grayscale images to obtain a plurality of facial emotion images;
the operation of inputting the first facial image into an emotion analysis model to obtain an emotion analysis result includes:
  inputting each of the facial emotion images into the emotion analysis model to obtain an emotion analysis probability of each of the facial emotion images; and
  obtaining the emotion analysis result according to a plurality of emotion analysis probabilities.

In an embodiment, before the operation of obtaining a first facial image, a benchmark human body parameter, and a human body posture analysis result of a target user, the method further includes:
  obtaining a plurality of facial image sets of the target user in the target built environment, each of the facial image sets including a plurality of second facial images;
  extracting, from each of the second facial images, a facial body parameter image corresponding to a region of interest of the human body parameter;
  performing green channel separation on each of the facial and human parameter images to obtain a green signal of interest corresponding to each of the facial image sets;
  preprocessing each of the green signals of interest to obtain an intermediate signal corresponding to each of the green signals of interest;
  determining a first wave peak in each of intermediate signals through a preset interval of number of heartbeats;
  obtaining an estimation value of the human body parameter corresponding to each of the facial image sets according to each of the first wave peaks; and
  obtaining the benchmark human body parameter of the target user according to a plurality of estimated values of the human body parameter.

In an embodiment, after the operation of obtaining the safe interval of the human body parameter of the target user according to the emotion analysis result, the human body posture analysis result, and the benchmark human body parameter, the method further includes:
  determining a second wave peak in each of the intermediate signals through the preset interval of number of heartbeats;
  obtaining a confidence ratio of each of the facial image sets according to the first wave peak and the second wave peak of each of the intermediate signals;
  obtaining an average value of the confidence ratio according to a plurality of confidence ratios; and
  determining the safety interval of the human body parameter as a final safety interval of the human body parameter when the average value of the confidence ratio is greater than a preset threshold.

In an embodiment, before the operation of obtaining a first facial image, a benchmark human body parameter, and a human body posture analysis result of a target user in a target built environment, the method further includes:
  obtaining a plurality of posture images of the target user in the target built environment;
  obtaining a plurality of key point coordinates corresponding to each of the posture images according to each of the posture images;
  obtaining a first human body angle and a second human body angle corresponding to each of the posture images according to the plurality of key point coordinates of each of the posture images;

obtaining initial human body posture information corresponding to each of the posture images according to the first human body angle, the second human body angle and a preset angle threshold of each of the posture images; and obtaining the human body posture analysis result according to the initial human body posture information.

In an embodiment, before the operation of obtaining the safe interval of the human body parameter of the target user according to the emotion analysis result, the human body posture analysis result, and the benchmark human body parameter, the method further includes:

obtaining a preset standard human body parameter interval corresponding to the target user;

determining a user type of the target user according to the preset standard human body parameter interval and the benchmark human body parameter;

the operation of obtaining the safe interval of the human body parameter of the target user according to the emotion analysis result, the human body posture analysis result, and the benchmark human body parameter includes:

obtaining an emotion floating parameter according to the user type and the emotion analysis result;

obtaining a movement floating parameter according to the user type and the human body posture analysis result; and obtaining the safe interval of the human body parameter of the target user according to the movement floating parameter, the emotion floating parameter, and the benchmark human body parameter.

In an embodiment, before the operation of obtaining a first facial image, a benchmark human body parameter, and a human body posture analysis result of a target user, the method further includes:

obtaining a facial video of the target user in the target built environment;

extracting the first facial image from the facial video when the facial video meets a preset condition;

when a selected preset facial image matching the first facial image exists in a preset facial image library, obtaining age information corresponding to the selected preset facial image from a preset information library; and determining a preset standard human body parameter interval corresponding to the target user in a preset human body parameter comparison table according to the age information.

Besides, in order to achieve the above objective, the present disclosure further provides a device for obtaining a safe interval of a human body parameter in a built environment, including:

an acquisition module for obtaining a first facial image, a benchmark human body parameter, and a human body posture analysis result of a target user in a target built environment;

an analysis module for inputting the first facial image into an emotion analysis model to obtain an emotion analysis result; and an obtaining module for obtaining the safe interval of the human body parameter of the target user according to the emotion analysis result, the human body posture analysis result, and the benchmark human body parameter.

Besides, in order to achieve the above objective, the present disclosure further provides a terminal device, including: a memory and a processor. Here, a program for obtaining a safe interval of a human body parameter in a built environment stored in the memory and executable on the processor, when the program is executed by the processor, the operations of the method for obtaining a safe interval of a human body parameter in a built environment as described above are implemented.

Besides, in order to achieve the above objective, the present disclosure further provides a non-transitory computer readable storage medium, where a program for obtaining a safe interval of a human body parameter in a built environment is stored in the non-transitory computer readable storage medium, when the program is executed by a processor, the operations of the method for obtaining a safe interval of a human body parameter in a built environment as described above are implemented.

The present disclosure provides a method for obtaining a safe interval of a human body parameter in a built environment, including: obtaining a first facial image, a benchmark human body parameter, and a human body posture analysis result of a target user in a target built environment; inputting the first facial image into an emotion analysis model to obtain an emotion analysis result; and obtaining the safe interval of the human body parameter of the target user according to the emotion analysis result, the human body posture analysis result, and the benchmark human body parameter.

In the present disclosure, when the user is in the same human body posture, the emotions are different, and the corresponding benchmark human body parameters are different. However, in the related art, for the same human body posture, the preset benchmark human body parameters are the same, which results in poor accuracy of the benchmark human body parameters. Using the method of the present disclosure, considering the influence of emotion on the human body parameter of the target user, based on the emotion analysis result, the human body posture analysis result and the benchmark human body parameter of the target user, the safety interval of the human body parameter is obtained. The safety interval of the human body parameter can take into account the emotion information of the target user, so that the accuracy of the safety interval of the human body parameter is higher.

BRIEF DESCRIPTION OF THE DRAWINGS

In order to more clearly illustrate the embodiments of the present disclosure, drawings used in the embodiments will be briefly described below. Obviously, the drawings in the following description are only some embodiments of the present disclosure. It will be apparent to those skilled in the art that other figures can be obtained according to the structures shown in the drawings without creative work.

The realization of the objective, functional characteristics, and advantages of the present disclosure are further described with reference to the accompanying drawings.

DETAILED DESCRIPTION OF THE EMBODIMENTS

The technical solutions of the embodiments of the present disclosure will be described in more detail below with reference to the accompanying drawings. It is obvious that the embodiments to be described are only some rather than all of the embodiments of the present disclosure. All other embodiments obtained by persons skilled in the art based on the embodiments of the present disclosure without creative efforts shall fall within the scope of the present disclosure.

Figure 1:
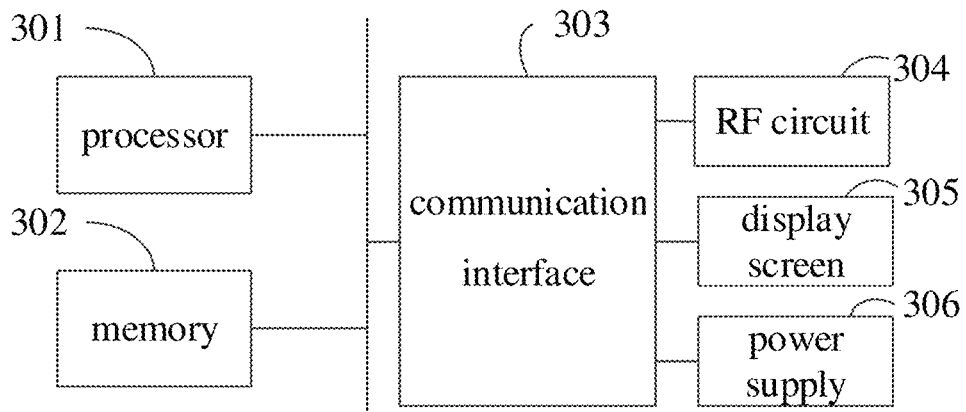
FIG. 1 is a schematic structural diagram of a terminal device in a hardware operating environment according to an embodiment of the present disclosure.

As shown in FIG. 1, FIG. 1 is a schematic structural diagram of a terminal device in a hardware operating environment according to an embodiment of the present disclosure.

Generally, a terminal device includes: at least one processor 301, a memory 302, and a program for obtaining a safe interval of a human body parameter in a built environment that is stored on the memory and can be run on the processor. The program for obtaining the safe interval of the human body parameter in the built environment is configured to implement the operations of the aforementioned method for obtaining the safe interval of the human body parameter in the built environment.

The processor 301 can include one or more processing cores, such as a 4-core processor, an 8-core processor, and so on. The processor 301 can be implemented in at least one hardware form among digital signal processing (DSP), field programmable gate array (FPGA), and programmable logic array (PLA). The processor 301 can also include a main processor and a coprocessor. The main processor is a processor configured to process data in the awake state, and is also called a central processing unit (CPU). The coprocessor is a low-power processor configured to process data in the standby state. In some embodiments, the processor 301 can be integrated with a graphics processing unit (GPU), and the GPU is used for rendering and drawing content that needs to be displayed on the display screen. The processor 301 can also include an artificial intelligence (AI) processor. The AI processor is configured to process the operation of the method for obtaining the safe interval of the human body parameter in the built environment, so that the safe interval obtaining method model of the human body parameter in the built environment can be independently trained and learned, and the efficiency and accuracy are improved.

The memory 302 can include one or more storage media, and the storage media can be non-transitory. The memory 302 can also include high-speed random access memory and non-volatile memory, such as one or more magnetic disk storage devices and flash memory storage devices. In some embodiments, the non-transitory storage medium in the memory 302 is configured to store at least one instruction. The at least one instruction is executed by the processor 301 to implement the method for obtaining the safety interval of the human body parameter in the built environment provided by the method embodiment of the present disclosure.

In some embodiments, the terminal can optionally further include: a communication interface 303 and at least one peripheral device. The processor 301, the memory 302, and the communication interface 303 can be connected by a bus or a signal line. Each peripheral device can be connected to the communication interface 303 through a bus, a signal line or a circuit board. Specifically, the peripheral device includes at least one of a radio frequency circuit 304, a display screen 305, and a power supply 306.

The communication interface 303 can be used to connect at least one peripheral device related to Input/Output (I/O) to the processor 301 and the memory 302. In some embodiments, the processor 301, the memory 302, and the communication interface 303 are integrated on the same chip or circuit board. In some other embodiments, any one or both of the processor 301, the memory 302, and the communication interface 303 can be implemented on a separate chip or circuit board, which is not limited in this embodiment.

The radio frequency circuit 304 is used for receiving and transmitting radio frequency (RF) signals, also called electromagnetic signals. The radio frequency circuit 304 is in communication with a communication network and other communication devices through electromagnetic signals. The radio frequency circuit 304 converts electrical signals into electromagnetic signals for transmission, or converts received electromagnetic signals into electrical signals. Optionally, the radio frequency circuit 304 includes: an antenna system, an RF transceiver, one or more amplifiers, a tuner, an oscillator, a digital signal processor, a codec chipset, a user identity module card, and so on. The radio frequency circuit 304 can communicate with other terminals through at least one wireless communication protocol. The wireless communication protocol includes, but is not limited to: metropolitan area networks, various generations of mobile communication networks (2G, 3G, 4G, and 5G), wireless local area networks and/or wireless fidelity (WiFi) networks. In some embodiments, the radio frequency circuit 304 can also include a circuit related to near field communication (NFC), which is not limited in the present disclosure.

The display screen 305 is configured to display a user interface (UI). The UI can include graphics, text, icons, videos, and any combination thereof. When the display screen 305 is a touch display screen, the display screen 305 also has the ability to collect the touch signal on or above the surface of the display screen 305. The touch signal can be input to the processor 301 as a control signal for processing. The display screen 305 can also provide virtual buttons and/or virtual keyboards, also called soft buttons and/or soft keyboards. In some embodiments, the display screen 305 can be a front panel of an electronic device. In other embodiments, there can be at least two display screens 305, which are respectively arranged on different surfaces of the electronic device or in a folded design. In still other embodiments, the display screen 305 can be a flexible display screen, which is provided on a curved surface or a folding surface of the electronic device. Furthermore, the display screen 305 can also be set as a non-rectangular irregular figure, that is, a special-shaped screen. The display screen 305 can be made of materials such as liquid crystal display (LCD), organic light-emitting diode (OLED), or the like.

The power supply 306 is configured to supply power to various components in the electronic device. The power supply 306 can be alternating current, direct current, a disposable battery, or a rechargeable battery. When the power supply 306 includes a rechargeable battery, the rechargeable battery can support wired charging or wireless charging. The rechargeable battery can also support fast charging technology.

Those skilled in the art should understand that the structure shown in FIG. 1 does not constitute a limitation on the terminal device, and can include more or fewer components, a combination of some components, or differently arranged components than shown in the figure.

Besides, the present disclosure further provides a storage medium. The storage medium stores a program for obtaining a safe interval of a human body parameter in a built environment. When the program for obtaining the safe interval of the human body parameter in the built environment is executed by the processor, the operations of the method for obtaining the safe interval of the human body parameter in the built environment as described above are realized. Therefore, it will not be repeated here. In addition, the description of the beneficial effects of using the same method will not be repeated. For technical details that are not disclosed in the storage medium embodiments involved in the present disclosure, please refer to the description of the method embodiments of the present disclosure. The program instructions can be executed by one terminal device, or executed by multiple terminal devices located in one location or distributed in multiple locations and interconnected by a communication network.

A person of ordinary skill in the art can understand that all or part of the processes in the method of the foregoing embodiments can be implemented by instructing relevant hardware through a computer program. The above-mentioned program can be stored in a storage medium, and when the program is executed, it can include the processes of the embodiments of the above-mentioned methods. The aforementioned storage medium can be a magnetic disk, an optical disc, a read-only memory (ROM), or a random access memory (RAM), or the like.

Based on the above hardware structure, an embodiment of the method for obtaining a safe interval of a human body parameter in a built environment of the present disclosure is proposed.

Figure 2:
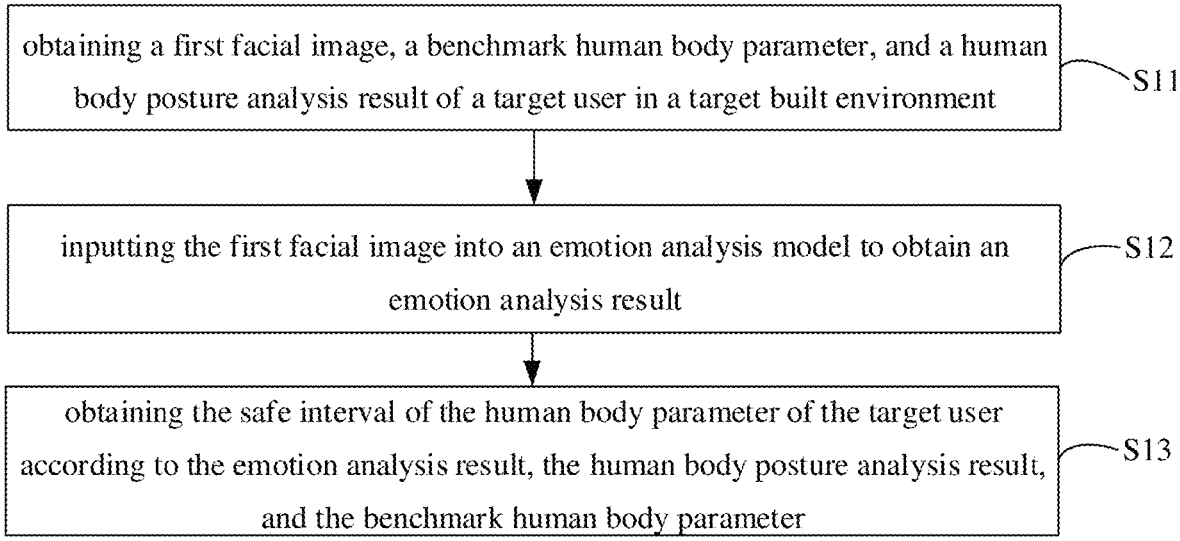
FIG. 2 is a schematic flowchart of a method for obtaining a safe interval of a human body parameter in a built environment according to a first embodiment of the present disclosure.

As shown in FIG. 2, FIG. 2 is a schematic flowchart of a method for obtaining a safe interval of a human body parameter in a built environment according to a first embodiment of the present disclosure. The method is applied to a terminal device, and the method includes the following operations.

Operation S11, obtaining a first facial image, a benchmark human body parameter, and a human body posture analysis result of a target user in a target built environment.

It should be noted that the execution subject of the present disclosure is a terminal device, and the terminal device is installed with a program for obtaining a safe interval of a human body parameter in a built environment. When the terminal device executes the program for obtaining the safe interval of the human body parameter in the built environment, the operations of the method for obtaining the safe interval of the human body parameter in the built environment of the present disclosure are implemented. Generally, the software for obtaining the safety interval of the human body parameter in the built environment has an interactive interface, and the operations of the present disclosure are implemented on the interactive interface. Generally, in the present disclosure, the terminal device is a personal computer or a computer, and the terminal device is connected to the face camera and the body camera respectively. The face camera is configured to capture facial video and send the facial video to the terminal device for subsequent processing, the human body camera is configured to capture the human body video and send the human body video to the terminal device for subsequent processing.

The target user is a user to be analyzed for the human body parameter. The benchmark human body parameter of the target user are the human body parameter when the target user is in a quiet state and does not carry any emotions. The human body posture analysis result when the target user obtains the safe interval of the human body parameter in the built environment is the human posture analysis result in operation S11. In the present disclosure, the human body parameter is mainly heart rate, and can also be blood sugar and blood pressure. The target built environment is a built environment where the target user is located, such as an office or a gymnasium.

Further, before the operation of obtaining a first facial image, a benchmark human body parameter, and a human body posture analysis result of a target user, the method further includes: obtaining a facial video of the target user in the target built environment; extracting the first facial image from the facial video when the facial video meets a preset condition; if a selected preset facial image matching the first facial image exist in a preset facial image library, obtaining age information corresponding to the selected preset facial image from a preset information library; and determining a preset standard human body parameter interval corresponding to the target user in a preset human body parameter comparison table according to the age information.

Meanwhile, if the selected preset facial image matching the first facial image does not exist in the preset facial image library, age information sent by the target user is received. Furthermore, the preset standard human body parameter interval corresponding to the target user is determined in the preset human body parameter comparison table according to the age information.

In the present disclosure, the facial video (for the sake of the distinction, the real-time facial video, the facial video to obtain the first facial image is called the first facial video) and the human body video are captured simultaneously, and their capturing duration is usually the same. For the first facial video of the target user, a start moment of the first facial video is taken as the starting point, and a first preset number of frames (the number of frames in 1 minute, usually 600 frames) is taken as a window, a second preset number of frames (usually 200 frames) is taken as a step size, to run the sliding window algorithm. If all video frames in a window include facial information, then the first facial video satisfies the preset condition, and there are a plurality of first facial images in all video frames in the window (the first facial images described below include multiple). If there are video frames that do not include facial information among all the video frames in the window, it is possible to move according to the step size corresponding to the second preset number of frames, and continue to filter, until it is determined that the first facial video meets the preset condition, the corresponding first facial image is obtained, or the first facial video does not meet the preset condition, the first facial video is re-acquired, and the filtering is continued.

The preset facial image library is a collection of user's facial images obtained by using the terminal device to perform the safety interval of the human body parameter in the built environment. When the user uses the terminal device to perform the method for obtaining the safe interval of the human body parameter in the built environment of the present disclosure, the preset information is inputted, the inputted preset information includes the facial image (the facial image can be obtained based on the first facial image, and no further acquisition is required), age, name, and so on. The facial image matching the first facial image (any one of the plurality of first facial images, because it is the same person) in the preset facial image library is the selected preset facial image.

When the selected preset facial image matching the first facial image exist in the preset facial image library, indicating that the target user is not a new user, and the preset information library contains the corresponding preset information. If the selected preset facial image matching the first facial image does not exist in the preset facial image library, indicating that the target user is a new user, and the corresponding preset information does not exist in the preset information library. The target user needs to input preset information. The inputted preset information includes the facial image (the facial image can be obtained based on the first facial video, and no further acquisition is required), age, name, and so on. The preset information library includes all inputted preset information.

When the selected preset facial image matching the first facial image exists in the preset facial image library, the selected preset facial image is used to determine the corresponding age information in the preset information library. The determined age information is the information of the target user.

As shown in Table 1, Table 1 is a schematic diagram of the preset human body parameter comparison table of the present disclosure, the human body parameter shown in the table 1 is the heart rate.

TABLE 1

| Age/years old | 0-1 | 1-3 | 3-6 | 6-12 | 12-14 | 14-16 | 16-18 | 18-65 | Over 65 |
|---|---|---|---|---|---|---|---|---|---|
| Lower limit/BPM | 80 | 80 | 75 | 70 | 65 | 60 | 55 | 60 | 70 |
| Upper limit/BPM | 160 | 120 | 115 | 110 | 105 | 100 | 95 | 100 | 100 |
| Average value/BPM | 120 | 100 | 100 | 90 | 85 | 80 | 75 | 72 | 75 |

BPM is the heart rate (unit: beats/min). A preset standard heart rate interval is an interval composed of an upper limit heart rate and a lower limit heart rate corresponding to the age information. For example, if the target user is 20 years old, the preset standard heart rate interval is [60, 100]. The purpose of the preset standard heart rate interval will be described below, which will not be repeated herein.

There can be different comparison tables for other types of human body parameters, which are not limited in the present disclosure, and users can set according to the mode of Table 1 based on their own needs.

It is understandable that the first facial image refers to the real-time capturing of the facial image corresponding to the first facial video of the target user when the method for obtaining the safe interval of the human body parameter in the built environment of the present disclosure is performed. In the facial video, the posture of the target user can be of various types, such as sitting posture, standing posture, or exercising.

Further, before the operation of obtaining a first facial image, a benchmark human body parameter, and a human body posture analysis result of a target user, the method further includes: obtaining a plurality of facial image sets of the target user in the target built environment, each of the facial image sets including a plurality of second facial images; extracting, from each of the second facial images, a facial body parameter image corresponding to a region of interest of the human body parameter; performing green channel separation on each of the facial and human parameter images to obtain a green signal of interest corresponding to each of the facial image sets; preprocessing each of the green signals of interest to obtain an intermediate signal corresponding to each of the green signals of interest; determining a first wave peak in each of the intermediate signals through a preset interval of number of heartbeats; obtaining an estimation value of the human body parameter corresponding to each of the facial image sets according to each of the first wave peaks; and obtaining the benchmark human body parameter of the target user according to a plurality of estimated values of the human body parameter.

The facial video where the target user is in a quiet state and does not carry any emotions (for the sake of distinction, this facial video is called the second facial video) is a facial video used to obtain the benchmark human body parameter. A start moment of the second facial video is taken as the starting point, and a first preset number of frames (the number of frames in 1 minute, usually 600 frames) is taken as a window, a second preset number of frames (usually 200 frames) is taken as a step size, to run the sliding window algorithm. If all video frames in a window include facial information, then the second facial video satisfies the preset condition to determine a plurality of second facial images in all video frames. If there are video frames that do not include facial information among all the video frames in the window, it is possible to move according to the step size corresponding to the second preset number of frames, and continue to filter, until it is determined that the second facial video meets the preset condition, the corresponding second facial image is obtained, or the facial video does not meet the preset condition, the second facial video is re-acquired, and the filtering is continued.

Every time the second facial video meets the preset condition, all the corresponding video frames are all the second facial images included in one facial image set. For each second facial image, it is necessary to calculate the human body parameter estimation value. The facial body parameter image corresponding to the region of interest on the human body parameter is locked through facial feature points. Specifically, the trained 68 facial key point detection module in the dlib library is used to lock facial feature points, the specific steps are:

predictor=dlib.shape_predictor
('shape_predictor_68_face_landmarks.dat')

Since the light absorption of hemoglobin is most sensitive to the oxygenation changes of green light, the green (G) channel in the RGB three channels of all facial body parameter images corresponding to a facial image set captured in the normal camera is separated to obtain the green signal of interest.

Figure 3:
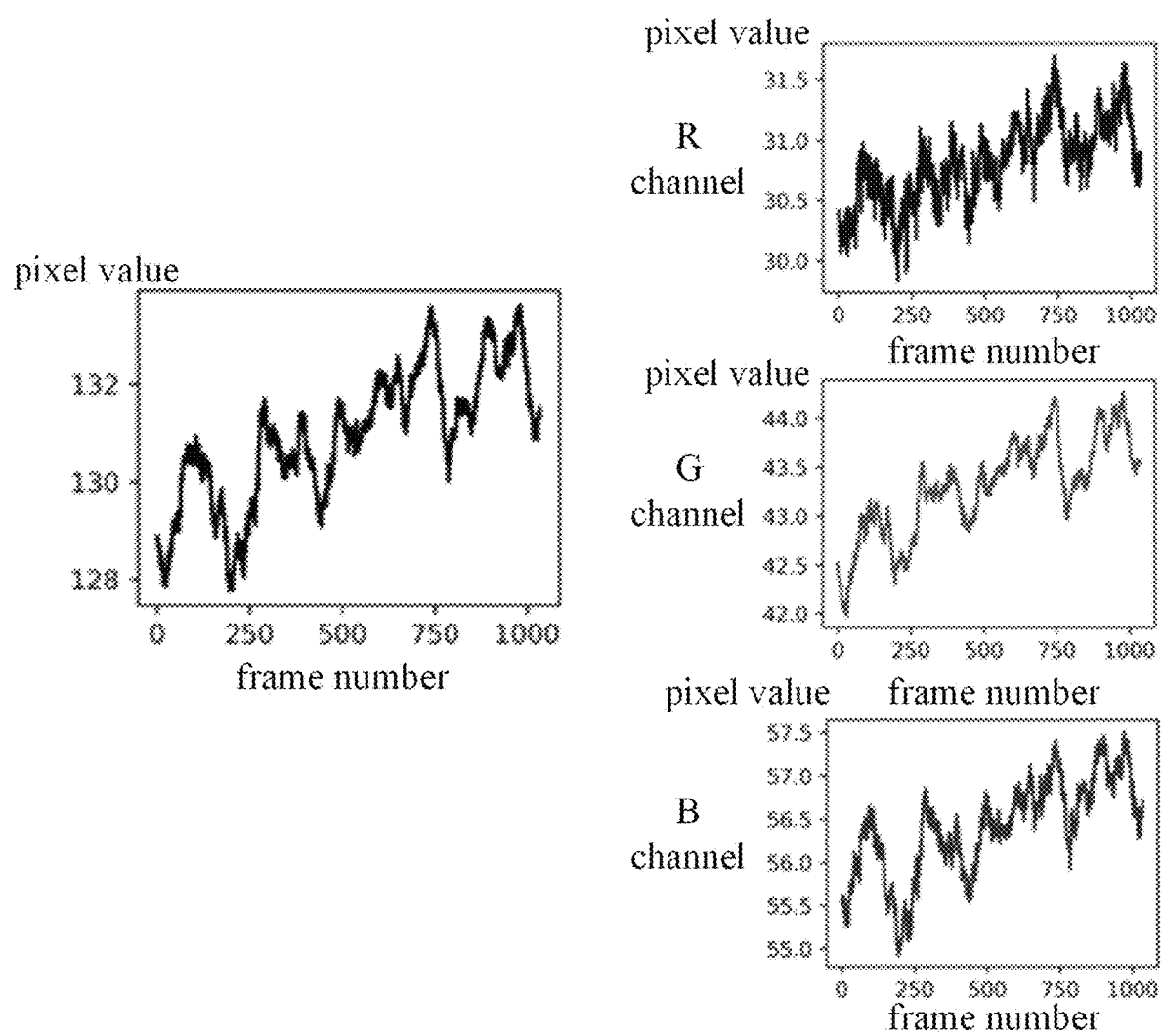
FIG. 3 is a waveform diagram of a green signal of interest of the present disclosure.

As shown in FIG. 3, FIG. 3 is a waveform diagram of the green signal of interest of the present disclosure, the picture on the left side of FIG. 3 is a waveform diagram corresponding to all facial body parameter images involved in the facial image set. On the right side of FIG. 3, the second image (G channel) from top to bottom is the waveform of the green signal of interest. In FIG. 3, the facial image meets the preset conditions for a continuous period of time (may be within 2 minutes). The number of frames in FIG. 3 exceeds 1000 consecutive frames, and can include waveforms corresponding to at least two facial image sets.

Then, it is necessary to perform pre-processing operations such as detrending, deaveraging, and normalizing the green signal of interest, and filter out the noise, then use Fast Fourier Transform (FFT) to convert the waveform of the green signal of interest to the frequency domain to obtain the intermediate signal. Specifically, the fftpack module in the scipy library is used for frequency domain conversion.

frequencies=fftpack.fftfreq(ROI_HR_G.shape[0], d=1.0/fps)

Then, it is necessary to filter the intermediate signal with a 0.8 Hz to 3 Hz (the corresponding human body parameter is 48 BPM to 180 BPM, which is the interval of preset heartbeat times) band-pass filter, and find the corresponding wave peaks of the intermediate signal that fall within the interval of preset heartbeat times (48 BPM to 180 BPM). The above operations can be achieved with the signal module in the scipy library, as follows:

peaks, properties=signal.find_peaks(frequencies)

Among the selected wave peaks, the highest wave peak is a first wave peak, and the second highest wave peak is a second wave peak. Then, the product of the frequency of the first wave peak and 60 is determined as a human body parameter estimation value corresponding to a facial image set, Then, according to the estimated values of all human body parameters in all facial image sets, the average value—the benchmark human body parameter of the target user is obtained, and the benchmark human body parameter is an average value of human body parameters.

Figure 4:
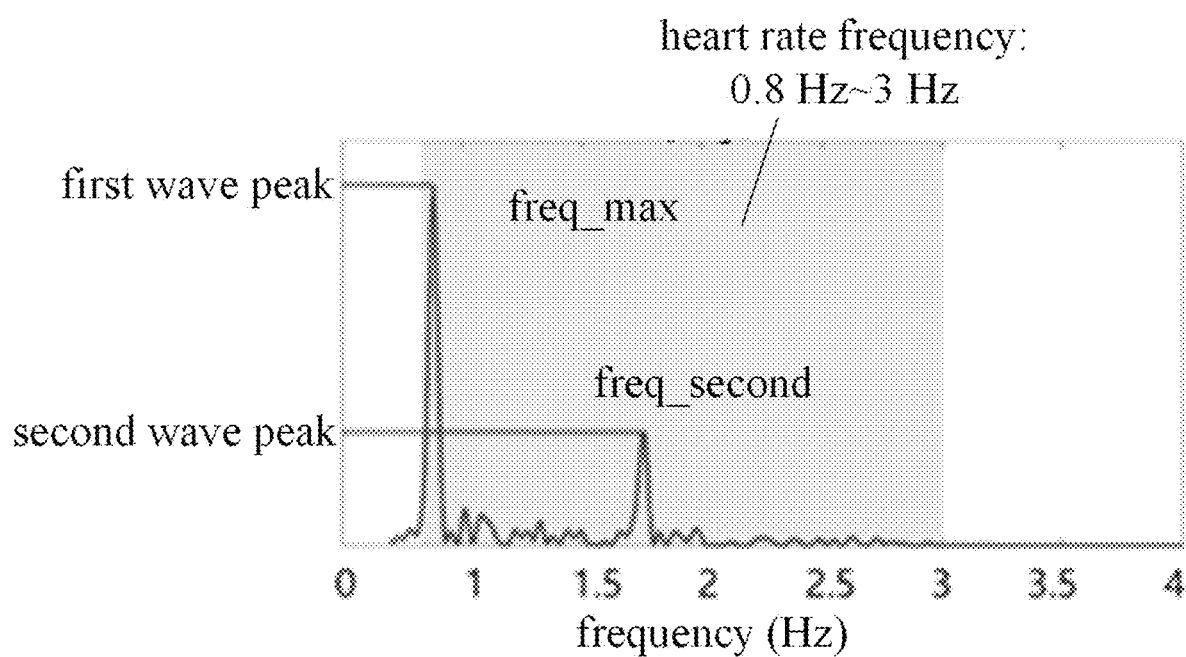
FIG. 4 is a schematic diagram of a first wave peak and a second wave peak of the present disclosure.

As shown in FIG. 4, FIG. 4 is a schematic diagram of the first wave peak and the second wave peak of the present disclosure. The highest wave peak in FIG. 4 is the first wave peak, and the second highest wave peak in FIG. 4 is the second wave peak.

The ratio of the value of the first wave peak to the value of the second wave peak is determined as the confidence ratio, and the average value—the average value of the confidence ratio is obtained according to the confidence ratios of all facial image sets. The average value of the confidence ratio is used for the credibility judgment of the benchmark human body parameters, and can also be further used for the credibility judgment of the safety interval of the human body parameters.

It is understandable that the second facial image refers to the facial image corresponding to a facial video taken when the target user is in a quiet state and does not carry any emotions when the method for obtaining the safe interval of the human body parameter in the built environment of the present disclosure is performed. In the facial video, the target user's state is a quiet state and does not carry any emotions, for example, sitting quietly without carrying any emotions.

Further, before the operation of obtaining a first facial image, a benchmark human body parameter, and a human body posture analysis result of a target user in a target built environment, the method further includes: obtaining a plurality of posture images of the target user in the target built environment; obtaining a plurality of key point coordinates corresponding to each of the posture images according to each of the posture images; obtaining a first human body angle and a second human body angle corresponding to each of the posture images according to the plurality of key point coordinates of each of the posture images; obtaining initial human body posture information corresponding to each of the posture images according to the first human body angle, the second human body angle and a preset angle threshold of each of the posture images; and obtaining the human body posture analysis result according to a plurality of the initial human body posture information.

The image corresponding to the posture of the target user when obtaining the safety interval of human body parameters in the building environment is the posture image, and multiple posture images need to be obtained (usually corresponding to the first facial image, for example, the first facial image is the facial image within the first minute of the first facial video, then the multiple posture images are also the posture images in the first minute of the human body video, and the shooting time of the first facial video and the human body video is the same). For each posture image, a lightweight 25 human body key point OpenPose model is used to recognize the posture image.

Figure 5:
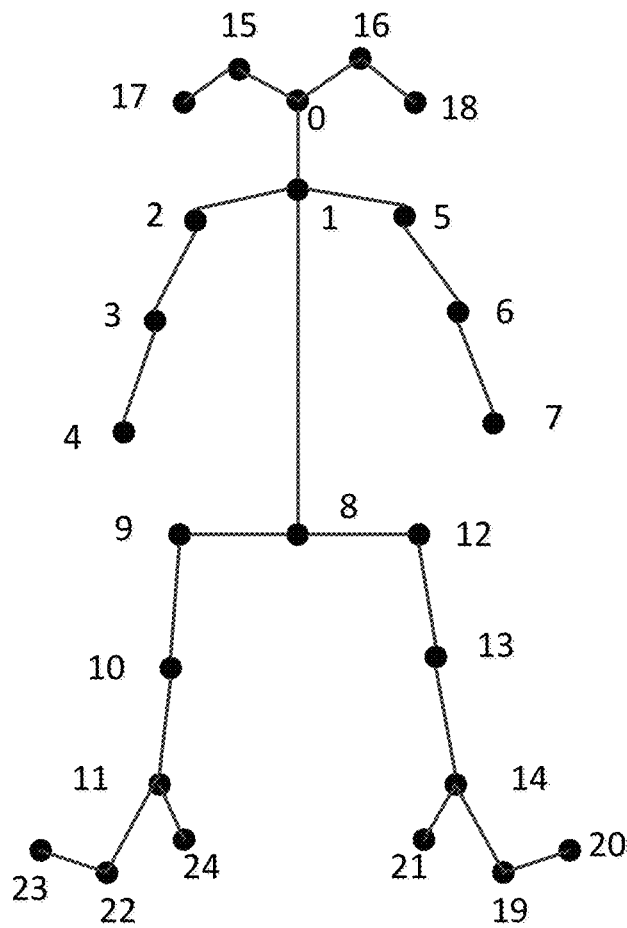
FIG. 5 is a schematic diagram of preset key points of the present disclosure.

As shown in FIG. 5, FIG. 5 is a schematic diagram of preset key points of the present disclosure. In FIG. 5, the preset key points corresponding to the human body include 25 key points, and multiple key points need to be determined among them. The determined multiple key points correspond to multiple key point coordinates, and one key point corresponds to one key point coordinate. The coordinates of 25 key points are 0 (nose), 1 (neck), 2 (right shoulder), 3 (right elbow), 4 (right wrist), 5 (left shoulder), 6 (left elbow), 7 (left wrist), 8 (middle hip), 9 (right hip), 10 (right knee), 11 (right ankle), 12 (left hip), 13 (left knee), 14 (left ankle), 15 (right eye), 16 (left eye), 17 (right ear), 18 (left ear), 19 (left thumb), 20 (left pinky), 21 (left heel), 22 (right thumb), 23 (right pinky) and 24 (right heel).

In an embodiment of the present disclosure, the multiple key points are the key points 1 (neck), 8 (middle hip), 12 (left hip), 13 (left knee) and 14 (left ankle) in FIG. 5. The corresponding key point coordinates are (x1, y1), (x8, y8), (x12, y12), (x13, y13) and (x14, y14). According to the key points 1 and 8 of the human body, the angle between the spine and the vertical direction—the trunk angle (the first human body angle) is calculated. According to the key points 12, 13, and 14, the angle between the thigh and the calf—the angle between the legs (the second human body angle) is calculated. The numpy and math libraries is used to calculate the first human body angle and the second human body angle, as follows:

$$\text{angle\_body} = abs(np.\arctan((x8-x1)/(y8-y1))*180/np.pi)$$

$$\cos\_leg = np.dot(s\_14\_13, s\_12\_13)/((math.sqrt((x14-x13)2+(y14-x13)2))*(math.sqrt((x12-x13)2+(y12-x13)2)))$$

$$\text{angle\_leg} = np.\arccos(B)*180/np.pi$$

Understandably, in the previous example, the five key points correspond to the left half of the body, and the five key points corresponding to the right half of the body are 1 (neck), 8 (middle hip), 9 (right hip), 10 (right knee), and 11 (right ankle).

In the present disclosure, the preset angle threshold includes two: trunk angle threshold (usually 60 degrees) and leg angle threshold (usually 150 degrees). If the first human body angle is greater than the trunk angle threshold, it is a sleeping posture. If the first human body angle is less than or equal to the trunk angle threshold, and the second human body angle is less than the leg angle threshold, then it is a sitting posture. In other cases, it is a standing posture, and the initial human body posture information is any one of these three posture information.

According to the above method, the initial human body posture information of each posture image is determined and then the proportion of various initial human body posture information in all the initial human body posture information is counted. The proportion of various initial human body posture information is the analysis result of the human body posture. That is, the human body posture analysis result may include the proportion of sitting posture, the proportion of standing posture, and the proportion of sleeping posture. It can be understood that the number of frames corresponds to the duration, and the proportion of the initial human body posture information corresponding to the posture image is the proportion of the number of frames and the proportion of the duration.

Operation S12, inputting the first facial image into an emotion analysis model to obtain an emotion analysis result.

When obtaining multiple first facial images of the target user (the first facial image is used for emotion recognition, and the second facial image is used for human parameter estimation—obtaining benchmark human parameters), and emotion analysis is performed using multiple first facial images.

Specifically, there are a plurality of the first facial images, before the operation of inputting the first facial image into an emotion analysis model to obtain an emotion analysis result, the method further includes: converting the plurality of first facial images into a plurality of grayscale images; extracting a facial emotion image corresponding to a region of interest of facial emotion from each of the grayscale images to obtain a plurality of facial emotion images; the operation of inputting the first facial image into an emotion analysis model to obtain an emotion analysis result includes: inputting each of the facial emotion images into the emotion analysis model to obtain an emotion analysis probability of each of the facial emotion images; and obtaining the emotion analysis result according to a plurality of emotion analysis probabilities.

Each first facial image corresponds to a grayscale image. In order to reduce the computation burden, a first facial image is converted into a grayscale image, and the MTCNN network is used to track the facial emotion region of interest for the grayscale image. Specifically, the library cv2 and mtcnn can be used for this operation:

gray_image_array=cv2.cvtColor(img, cv2.COLOR_BGR2GRAY)
results=self._mtcnn.detect_faces(gray_image_array)

The part corresponding to the facial emotion area of interest obtained after tracking is the facial emotion image, and the emotion analysis model stored in the local is retrieved and analyzed, for example, emotion_model.hdf5 is called for analysis, as follows:

emotion_model=pkg_resources.resource_filename("fer", "data/emotion_model.hdf5").

The output of the emotion analysis model is the probability of being happy or angry:

emotion_prediction=self._emotion_classifier.predict (gray_face)[0]

It is possible to obtain emotion information based on the probability of being happy or angry of a first facial image. If the probability of being happy or angry is higher than 50%, the frame is determined to be emotional. If the probability of being happy or angry is not higher than 50%, it is determined that the frame is not excited.

A plurality of emotion information corresponding to the plurality of first facial images are obtained according to the above method, the proportion of each emotion information is determined, and the proportion of each emotion information is the emotional analysis result. That is, the emotion analysis results may include the proportion of excited emotions or the proportion of non-excited emotions. It can be understood that the number of frames corresponds to the duration, and the proportion of emotion information corresponding to the first facial image is the proportion of the number of frames and the proportion of the duration.

Operation S13, obtaining the safe interval of the human body parameter of the target user according to the emotion analysis result, the human body posture analysis result, and the benchmark human body parameter.

In the present disclosure, the emotion analysis result is added to obtain the corresponding human body parameter safety interval, and the human body parameter safety interval can more accurately reflect the real health condition of the target user.

Before the operation of obtaining the safe interval of the human body parameter of the target user according to the emotion analysis result, the human body posture analysis result, and the benchmark human body parameter, the method further includes: obtaining a preset standard human body parameter interval corresponding to the target user; determining a user type of the target user according to the preset standard human body parameter interval and the benchmark human body parameter; the operation of obtaining the safe interval of the human body parameter of the target user according to the emotion analysis result, the human body posture analysis result, and the benchmark human body parameter includes: obtaining an emotion floating parameter according to the user type and the emotion analysis result; obtaining a movement floating parameter according to the user type and the human body posture analysis result; and obtaining the safe interval of the human body parameter of the target user according to the movement floating parameter, the emotion floating parameter, and the benchmark human body parameter.

Referring to the above description, according to the age information of the target user, the corresponding preset standard human body parameter interval is obtained. If the benchmark human body parameter is within the range corresponding to the preset standard human body parameter, the user type of the target user is a normal user, otherwise the user type of the target user is a risk user.

Specifically, if the proportion of excitement exceeds 50%, the emotion fluctuation parameter=1.116 (normal user), the emotion fluctuation parameter=1.068 (risk user). If the proportion of excitement does not exceed 50%, emotion fluctuation parameter=1 (risk user is the same as normal user). If the sleeping posture has the highest proportion: motion amplitude parameter=0.8 (normal user), motion amplitude parameter=0.95 (risk user). If the sitting posture has the highest proportion, motion amplitude parameter=1 (risk user is the same as normal user). If the standing posture has the highest proportion: motion amplitude parameter=1.2 (normal user), motion amplitude parameter=1.05 (risk user).

According to the motion amplitude parameter, the emotion fluctuation parameter and the benchmark human body parameter, the human body parameter safety interval of the target user is obtained. The upper limit value of the safety interval of human body parameter=benchmark human body parameter×1.1×motion amplitude parameter×emotion fluctuation parameter. The lower limit of the safety interval of human body parameter=benchmark human body parameter×0.9×motion amplitude parameter×emotion fluctuation parameter.

Further, after the operation of obtaining the safe interval of the human body parameter of the target user according to the emotion analysis result, the human body posture analysis result, and the benchmark human body parameter, the method further includes: determining a second wave peak in each of the intermediate signals through the preset interval of number of heartbeats; obtaining a confidence ratio of each of the facial image sets according to the first wave peak and the second wave peak of each of the intermediate signals; obtaining an average value of the confidence ratio according to a plurality of confidence ratios; and determining the safety interval of the human body parameter as a final safety interval of the human body parameter when the average value of the confidence ratio is greater than a preset threshold. The preset threshold can be set by the user based on requirements, which is not limited in the present disclosure, for example, the preset threshold is 3.

Usually, the final safety interval of the human body parameter has better accuracy and has more reference value, and when the average confidence ratio is less than or equal to the preset threshold, the accuracy of the safety interval of the human parameter is slightly weaker and the reference value is slightly lower.

It should be noted that, the present disclosure is based on the first facial video shot synchronously with the human body video. The start moment of the first facial video is taken as a starting point, and the first preset frame number (the number of frames in 1 minute, usually 600 frames) is taken as a window, the second preset number of frames (usually 200 frames) is taken as the step size, to run the sliding window algorithm. When all video frames in a window selection include face information, then the first facial video satisfies the preset condition, and is determined to be a plurality of third facial images (usually the plurality of first facial images determined above) in all the video frames. If there are video frames that do not include face information in all the video frames in the window selection, it is possible to move according to the step size corresponding to the second preset number of frames, and continue to filter, until it is determined that the first facial video satisfies the preset condition, a plurality of corresponding third facial images are obtained, or the first facial video does not satisfy the preset condition, the first facial video is reacquired, and the screening continues.

For each facial video that satisfies the preset condition, a third facial image set is determined to obtain a plurality of third facial image sets. Then, the real-time human body parameters of the target user-target human body parameters are obtained according to the method for obtaining the benchmark human body parameter and a plurality of third face image sets.

In the present disclosure, the benchmark human body parameter of the target user can be obtained in the above-mentioned manner, and the benchmark human body parameter of the target user is stored in the preset information database. That is, the preset information in the preset information library may include the benchmark human body parameters of historical users.

Then, it is possible to continue to obtain the human body parameter monitoring result of the target user according to the human body parameter safety interval and the target human body parameter.

Specifically, referring to the above description, the mean value of confidence ratio is also obtained, and the mean value of confidence ratio represents the reliability of the safety interval of human body parameter. Therefore, in some embodiments, the operation of the human body parameter monitoring result of the target user according to the human body parameter safety interval and the target human body parameter includes: obtaining the human body parameter monitoring result of the target user according to the human body parameter safety interval, the target human body parameter and the average value of the confidence ratio.

The specific methods for obtaining the monitoring result of the human body parameter are as follows. If the target human body parameter is within the safety interval of the human body parameter, the target user's human body parameter is in the normal range, the target user is not in an abnormal health state, and no alarm is sent. If the target human body parameter is not within the safety interval of the human body parameter, and the mean confidence ratio is less than or equal to 3 (the target human body parameter has low confidence), it is possible to output the prompt message "The system has detected abnormal human body parameters of the target user (target user name), and it is recommended to confirm it with a professional human body parameter measuring instrument", and send the prompt message to the family member or doctor corresponding to the target user for prompting. If the target human body parameter is not within the safety interval of the human body parameter, and the mean confidence ratio is greater than 3 (the target human body parameter has high confidence), it is possible to output the early warning information "The system has detected abnormal human parameters of the target user (target user name), and it is recommended to seek medical treatment or medication in time", and send the warning information to the family or doctor corresponding to the target user for early warning. The above prompt information and early warning information can be output on the interactive interface of the present disclosure.

For example, user Zhang San, 17 years old, the benchmark heart rate is 98, according to Table 1, the user is determined to be a risk user. Zhang San sat on the sofa and watched TV comfortably. After the camera (camera used to capture facial video) continuously captures the face information of Zhang San for more than 1 min (the facial video meets the preset conditions, because the face is continuously captured). By extracting the green channel signal of the facial image, Zhang San's average heart rate (target heart rate) in that minute was calculated as 116 BPM, with a mean pre-confidence ratio of 2.1 (low confidence). Through the facial image, it is predicted that Zhang San is in a happy state for more than 50% of the time in that minute, and the emotion floating parameter is 1.068. Through the posture image, it is determined that Zhang San's posture is in the sitting posture most of the time during the minute, and the motion floating parameter is 1. Then, the safe heart rate interval of Zhang San in this minute is calculated as [94, 115], and the target heart rate and the mean confidence ratio are combined to judge that Zhang San's heart rate is not in the normal range, and output the prompt message "The system has detected abnormal heart rate of user Zhang San, it is recommended to confirm with a professional heart rate measuring instrument", and send the prompt message to the family member or doctor corresponding to the target user for prompting.

For example, user Li Si, 36 years old, the benchmark heart rate is 68, according to Table 1, the user is determined to be a normal user. Li Si stood up and called angrily. After the camera (camera used to capture facial video) continuously captures the face information of Li Si for more than 1 min (the facial video meets the preset conditions, because the face is continuously captured). By extracting the green channel signal of the facial image, Li Si's average heart rate (target heart rate) in that minute was calculated as 97 BPM, with a mean pre-confidence ratio of 4.7 (high confidence). Through the facial image, it is predicted that Li Si is in an angry state for more than 50% of the time in this minute, and the emotion floating parameter is 1.116. Through the posture image, it is determined that Li Si's posture is in a standing posture most of the time in this minute, and the motion floating parameter is 1.2. Then, the safe heart rate interval of Li Si in that minute is calculated as [82,100]. The two parameters of target heart rate and confidence ratio mean are combined to determine that Li Si's heart rate is in the normal range, and no warning information or prompt information is sent.

The present disclosure provides a method for obtaining a safe interval of a human body parameter in a built environment, including following operations: obtaining a first facial image, a benchmark human body parameter, and a human body posture analysis result of a target user in a target built environment; inputting the first facial image into an emotion analysis model to obtain an emotion analysis result; and obtaining the safe interval of the human body parameter of the target user according to the emotion analysis result, the human body posture analysis result, and the benchmark human body parameter.

In the present disclosure, when the user is in the same human body posture, the emotions are different, and the corresponding benchmark human body parameters are different. However, in the related art, for the same human body posture, the preset benchmark human body parameters are the same, which results in poor accuracy of the benchmark human body parameters. Using the method of the present disclosure, considering the influence of emotion on the human body parameter of the target user, based on the emotion analysis result, the human body posture analysis result and the benchmark human body parameter of the target user, the safety interval of the human body parameter is obtained. The safety interval of the human body parameter can take into account the emotion information of the target user, so that the accuracy of the safety interval of the human body parameter is higher.

The method of the present disclosure adopts non-contact measurement of human body parameters, and compared with the existing contact-type human parameter monitoring equipment, the method of the present disclosure effectively avoids the potential safety hazard caused by the contact-type human parameter monitoring equipment, and is suitable for children, the elderly and people who have allergic reactions to the contact-type human parameter monitoring equipment.

Figure 6:
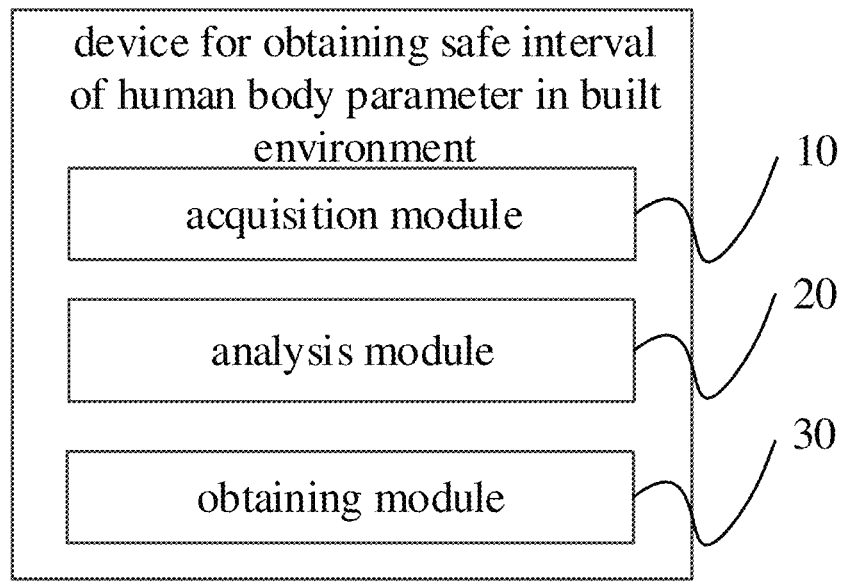
FIG. 6 is a structural block diagram of a device for obtaining a safe interval of a human body parameter in a built environment according to a first embodiment of the present disclosure.

As shown in FIG. 6, FIG. 6 is a structural block diagram of a device for obtaining a safe interval of a human body parameter in a built environment according to a first embodiment of the present disclosure. The device is applied to a terminal device. Based on the same inventive concept as the previous embodiment, the device includes:

an acquisition module 10 for obtaining a first facial image, a benchmark human body parameter, and a human body posture analysis result of a target user in a target built environment;

an analysis module 20 for inputting the first facial image into an emotion analysis model to obtain an emotion analysis result; and an obtaining module 30 for obtaining the safe interval of the human body parameter of the target user according to the emotion analysis result, the human body posture analysis result, and the benchmark human body parameter.

It should be noted that, since the operations performed by the device of this embodiment are the same as the operations of the foregoing method embodiments, the specific implementation manner and the technical effects that can be achieved can be referred to the foregoing embodiments, which will not be repeated herein.

The above are only some embodiments of the present disclosure, and do not limit the scope of the present disclosure thereto. Under the inventive concept of the present disclosure, equivalent structural transformations made according to the description and drawings of the present disclosure, or direct/indirect application in other related technical fields are included in the scope of the present disclosure.

What is claimed is:

1. A method for obtaining a safe interval of a human body parameter in a built environment, comprising the following operations:

obtaining a first facial image, a benchmark human body parameter, and a human body posture analysis result of a target user in a target built environment;

inputting the first facial image into an emotion analysis model to obtain an emotion analysis result; and obtaining the safe interval of the human body parameter of the target user according to the emotion analysis result, the human body posture analysis result, and the benchmark human body parameter, wherein before the operation of obtaining the first facial image, the benchmark human body parameter, and the human body posture analysis result of the target user in the target built environment, the method further comprises:

obtaining a plurality of posture images of the target user in the target built environment;

obtaining a plurality of key point coordinates corresponding to each of the posture images;

obtaining a first human body angle and a second human body angle corresponding to each of the posture images according to the plurality of key point coordinates of each of the posture images;

obtaining initial human body posture information corresponding to each of the posture images according to the first human body angle, the second human body angle and a preset angle threshold of each of the posture images; and obtaining the human body posture analysis result according to the initial human body posture information.

2. The method of claim 1, wherein there are a plurality of first facial images, before the operation of inputting the first facial image into the emotion analysis model to obtain the emotion analysis result, the method further comprises:

converting the plurality of first facial images into a plurality of grayscale images; and extracting a facial emotion image corresponding to a region of interest of facial emotion from each of the grayscale images to obtain a plurality of facial emotion images;

wherein the operation of inputting the first facial image into the emotion analysis model to obtain the emotion analysis result comprises:

inputting each of the facial emotion images into the emotion analysis model to obtain an emotion analysis probability of each of the facial emotion images; and obtaining the emotion analysis result according to a plurality of emotion analysis probabilities.

3. The method of claim 1, wherein before the operation of obtaining the first facial image, the benchmark human body parameter, and the human body posture analysis result of the target user, the method further comprises:
obtaining a plurality of facial image sets of the target user in the target built environment, each of the facial image sets including a plurality of second facial images;
extracting, from each of the second facial images, a facial body parameter image corresponding to a region of interest of the human body parameter;
performing green channel separation on each of the facial body parameter images to obtain a green signal of interest corresponding to each of the facial image sets;
preprocessing each of the green signals of interest to obtain an intermediate signal corresponding to each of the green signals of interest;
determining a first wave peak in each of the intermediate signals through a preset interval of a number of heartbeats;
obtaining an estimation value of the human body parameter corresponding to each of the facial image sets according to each of the first wave peaks; and
obtaining the benchmark human body parameter of the target user according to a plurality of estimated values of the human body parameter.

4. The method of claim 3, wherein after the operation of obtaining the safe interval of the human body parameter of the target user according to the emotion analysis result, the human body posture analysis result, and the benchmark human body parameter, the method further comprises:
determining a second wave peak in each of the intermediate signals through the preset interval of the number of heartbeats;
obtaining a confidence ratio of each of the facial image sets according to the first wave peak and the second wave peak of each of the intermediate signals;
obtaining an average value of the confidence ratio according to a plurality of confidence ratios; and
determining the safety interval of the human body parameter as a final safety interval of the human body parameter when the average value of the confidence ratio is greater than a preset threshold.

5. The method of claim 1, wherein before the operation of obtaining the safe interval of the human body parameter of the target user according to the emotion analysis result, the human body posture analysis result, and the benchmark human body parameter, the method further comprises:
obtaining a preset standard human body parameter interval corresponding to the target user; and
determining a user type of the target user according to the preset standard human body parameter interval and the benchmark human body parameter;
wherein the operation of obtaining the safe interval of the human body parameter of the target user according to the emotion analysis result, the human body posture analysis result, and the benchmark human body parameter comprises:
obtaining an emotion floating parameter according to the user type and the emotion analysis result;
obtaining a movement floating parameter according to the user type and the human body posture analysis result; and
obtaining the safe interval of the human body parameter of the target user according to the movement floating parameter, the emotion floating parameter, and the benchmark human body parameter.

6. The method of claim 5, wherein before the operation of obtaining the first facial image, the benchmark human body parameter, and the human body posture analysis result of the target user, the method further comprises:
obtaining a facial video of the target user in the target built environment;
extracting the first facial image from the facial video when the facial video meets a preset condition;
when a selected preset facial image matching the first facial image exists in a preset facial image library, obtaining age information corresponding to the selected preset facial image from a preset information library; and
determining the preset standard human body parameter interval corresponding to the target user in a preset human body parameter comparison table according to the age information.

7. A terminal device, comprising: a memory and a processor, wherein a program for obtaining a safe interval of a human body parameter in a built environment is stored in the memory and executable on the processor, when the program is executed by the processor, the operations of the method for obtaining the safe interval of the human body parameter in the built environment according to claim 1 are implemented.

8. A non-transitory computer readable storage medium, wherein a program for obtaining a safe interval of a human body parameter in a built environment is stored in the non-transitory computer readable storage medium, when the program is executed by a processor, the operations of the method for obtaining the safe interval of the human body parameter in the built environment according to claim 1 are implemented.

* * * * *